United States Patent
Schunk et al.

(10) Patent No.: US 7,045,144 B2
(45) Date of Patent: May 16, 2006

(54) PLASTER CONTAINING AN ACTIVE AGENT

(75) Inventors: Werner Schunk, Gotha (DE); Michael Bruder, Hamburg (DE); Konrad Giessmann, Gotha (DE); Karl-Heinz Krause, Chemnitz (DE); Gerhard Merkmann, Gotha (DE)

(73) Assignee: Intech Thüringen GmbH, Walterhausen (DE)

( * ) Notice: Subject to any disclaimer, the term of this patent is extended or adjusted under 35 U.S.C. 154(b) by 661 days.

(21) Appl. No.: 10/239,041

(22) PCT Filed: Feb. 23, 2001

(86) PCT No.: PCT/DE01/00687

§ 371 (c)(1),
(2), (4) Date: Sep. 18, 2002

(87) PCT Pub. No.: WO01/70202

PCT Pub. Date: Sep. 27, 2001

(65) Prior Publication Data

US 2003/0032909 A1    Feb. 13, 2003

(30) Foreign Application Priority Data

Mar. 20, 2000   (DE) ............................... 100 13 504

(51) Int. Cl.
*A61K 9/00*   (2006.01)
*A61K 9/70*   (2006.01)
*A61F 13/00*  (2006.01)

(52) U.S. Cl. .................... 424/447; 424/400; 424/443; 424/448; 424/449

(58) Field of Classification Search ............... 424/400, 424/443, 447, 448, 449
See application file for complete search history.

(56) References Cited

FOREIGN PATENT DOCUMENTS

| DD | 278 494 A | * | 5/1990 |
| DE | 278 492 | | 5/1990 |
| DE | 278 494 | | 5/1990 |

* cited by examiner

*Primary Examiner*—Michael Hartley
*Assistant Examiner*—Simon J. Oh
(74) *Attorney, Agent, or Firm*—Collard & Roe, P.C.

(57) ABSTRACT

The invention relates to a plaster containing an active agent, comprising at least one cover membrane and an active membrane which is based on a skin-compatible matrix containing a molecular sieve which is loaded with at least one active agent. The molecular sieve/active agent adduct releases the active agent when the active membrane comes into contact with the skin, in conjunction with the transpired water of the skin. The inventive plaster is characterised in that the molecular sieve/active agent adduct also contains water of crystallisation, to the extent that the molecular sieve is partially hydrated compared to a sufficient basic molar quantity (m) of water of crystallisation, the molecular sieve with the reduced molar quantity (m') of water of crystallisation being loaded with the active agent ($Z$, $Z_1$, $Z_2$) so that when the active membrane comes into contact with the skin, water is absorbed and the active agent is desorbed, whereupon the water of crystallisation content of the molecular sieve increases. The invention also relates to various suitable embodiments of the plaster containing an active agent and to an advantageous method for producing the inventive plaster containing an active agent.

21 Claims, 2 Drawing Sheets

PLASTER CONTAINING AN ACTIVE AGENT

CROSS REFERENCE TO RELATED APPLICATIONS

Applicants claim priority under 35 U.S.C. §119 of German Application No. 100 13 504.8 filed Mar. 20, 2000. Applicants also claim priority under 35 U.S.C. §365 of PCT/DE01/00687 filed Feb. 23, 2001. The international application under PCT article 21(2) was not published in English.

The invention relates to a plaster containing an active agent comprising at least
  one cover membrane and
  an active membrane based on a skin-compatible matrix containing a molecular sieve which is loaded with at least one active agent, wherein the molecular sieve/active agent adduct releases the active agent when the active membrane comes into contact with the skin, in conjunction with the transpired water of the skin.

Such a plaster containing an active agent is described in, for example East German Patent 278494 A1. The active membrane therein is formed, in particular, from a skin-compatible, pressure-sensitive adhesive, in which the molecular sieve/active agent adduct is incorporated. From this complex, the active agent is released by desorption, caused by diffusion of transpired water of the skin into the pressure-sensitive adhesive. Thereafter the active agent is dissolved and diffuses to the surface of the skin as a function of the composition of the pressure-sensitive adhesive.

The following advantages are associated with the use of plasters containing an active agent in connection with medical treatment:
  Plasters containing an active agent offer an effective alternative to ointment dressings.
  Plasters containing an active agent broaden the therapy spectrum in medicine considerably, especially in dermatology.
  Prolonged application of plasters containing an active agent is often more favorable than injections or tablets. Thus they embody a modern form of "transdermal systems".
  Since the active membrane adheres gently, the external irritations of adhesive bandages are eliminated. Nevertheless, a firm hold is ensured, in turn leading to good application. These advantages are evident, in particular, in the treatment of children.

In connection with a further development, the object of the invention is to provide a plaster containing an active agent that satisfies the following criteria:
  A high active agent concentration directly at the disease focus, with continuous active agent supply must be ensured. In the plasters containing an active agent known heretofore, either an "injection effect" occurred, i.e. the active agent level drops rapidly, accompanied by a substantial reduction of the time-release effect of the medication, or the active agent was released at an uncontrolled rate.
  The plaster containing an active agent must also be distinguished by improved penetration behavior in a moist environment. This is important in that the moist environment creates ideal conditions for cell growth factors and serves for immune defense.
  Furthermore, shorter treatment times at lower medication loads must be achieved with the plaster containing an active agent, together with simplified monitoring without clinical instruction.
  Finally, in dermatology, for example, the spectrum of medical applications must be broadened with the plaster containing an active agent, since some skin diseases (granulomas, keratoses) can only be treated with plasters containing an active agent.

For the purpose of achieving this object, the inventive plaster containing an active agent is now characterized according to the body of claim 1 in that
  the molecular sieve/active-agent adduct also contains water of crystallization, to the extent that the molecular sieve is partially dehydrated compared to a sufficient basic molar quantity (m) of water of crystallization, said molecular sieve with the reduced molar quantity (m') of water of crystallization being loaded with the active agent, so that when the active membrane comes into contact with the skin, water is adsorbed and the active agent is desorbed, whereupon the water of crystallization content of the molecular sieve increases.

Practical alternative embodiments of the plaster containing an active agent are specified in claims 2 through 19.

Another object of the invention is to provide a method for production of the inventive plaster containing an active agent.

According to the characteristics of claim 20, the method for production of the new plaster containing an active agent is now characterized by the following steps:
  the molecular sieve with a sufficient basic molar quantity (m) of water of crystallization is partially dehydrated at 300 to 500° C., preferably 400 to 450° C., for several hours, preferably 2 to 6 hours;
  the partially dehydrated molecular sieve with the reduced molar quantity (m') of water of crystallization is then loaded with at least one active agent, thereby forming the molecular sieve/active agent adduct;
  the molecular sieve/active agent adduct is now incorporated into the matrix to form the active membrane;
  finally, the active membrane is assembled with the cover membrane to form the plaster containing an active agent.

The foregoing dehydration and/or loading step(s) are/is performed, in particular, in the presence of an inert gas, such as nitrogen. The dehydration and/or loading step(s) are/is preferably performed under normal pressure. The loading step itself can be accomplished by means of a ball mill, for example.

Advantageously, the assembly step is followed by a drying process, which is carried out at 30 to 100° C., preferably 50 to 70° C., for 2 to 6 hours, preferably 3 to 4 hours. In this way, a self-adhesive matrix is formed.

Alternatively, the molecular sieve/active agent adduct can be prepared in such a way that, in combination with a non-adhesive matrix, it triggers the self-adhesive capability of the active membrane.

The invention will now be explained on the basis of exemplary embodiments with reference to schematic drawings, wherein.

Figure 1:
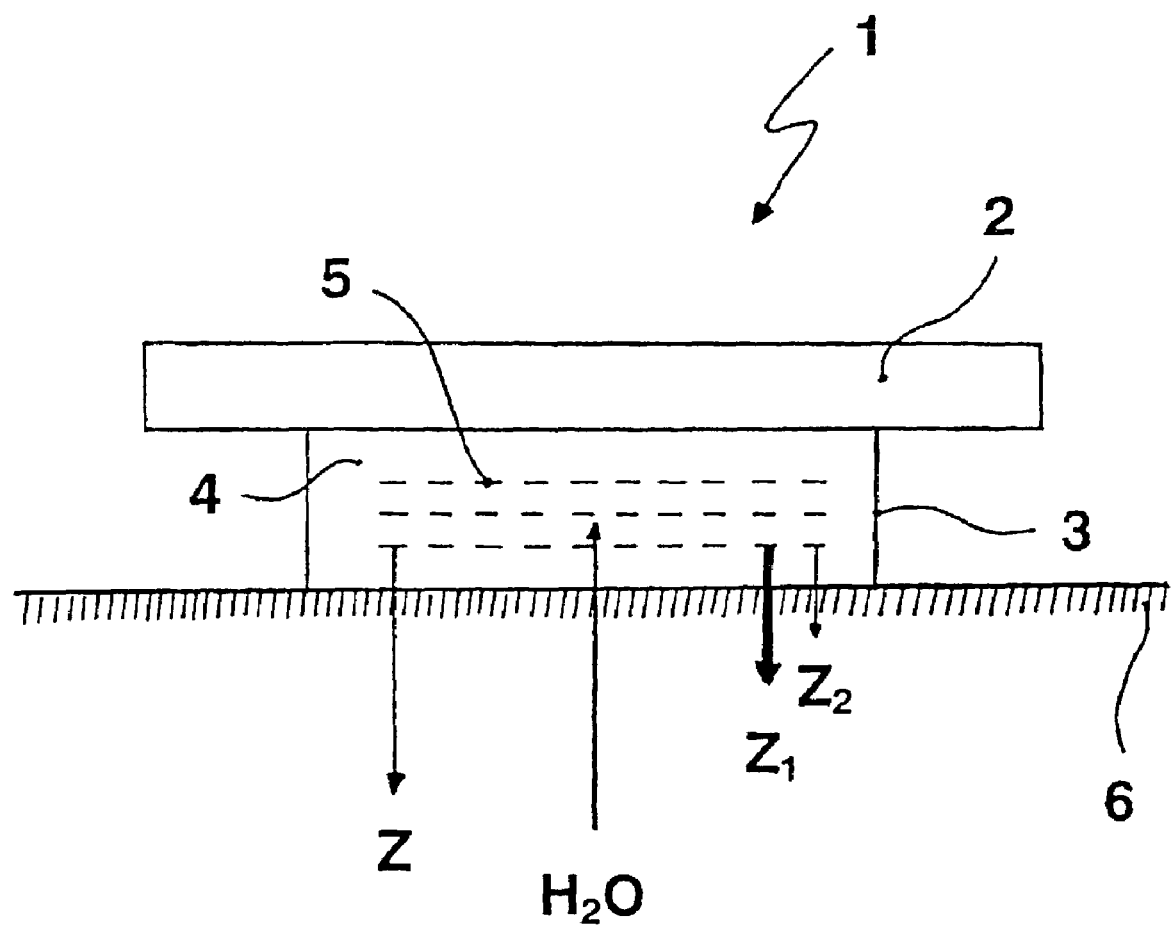
FIG. 1 shows the adsorption/desorption mechanism on the basis of two exemplary embodiments.

According to FIG. 1, plaster 1 containing an active agent has the form of a composite comprising a cover membrane 2 and a self-adhesive active membrane 3.

Active membrane 3 in turn comprises matrix 4, in which molecular sieve/active agent adduct 5 is incorporated. In particular, a sodium aluminosilicate of the formula $$Na_{86}[(AlO_2)_{86} \cdot (SiO_2)_{106}] \cdot m(m')H_2O$$

which contains a basic molar quantity (m=276) of water of crystallization in the not yet dehydrated state is used as the molecular sieve. During the partial dehydration step, at least 20%, preferably 40 to 70% of the moles of water are removed. The partially dehydrated molecular sieve with the reduced molar quantity (m'; for example, m'=200) is now loaded with an active agent Z.

During skin contact 6 of active membrane 3, water is now drawn from the skin or from the wound region and taken up (adsorption) by molecular sieve/active agent adduct 5, whereupon desorption of active agent Z takes place. At the same time, the content of water of crystallization in the molecular sieve increases. Thus the molecular sieve regains the water of crystallization that had been removed from it by partial dehydration.

The fact that molecular sieve/active agent adduct 5 basically contains water of crystallization ensures an appropriate moist environment. In this way, desorption of active agent Z by means of water acting as a solvent or dispersant agent is facilitated. In addition, the moist environment creates ideal conditions for cell growth factors and also serves for immune defense.

Examples of plasters containing an active agent are:
plaster containing prednisolone as the active agent (to counter inflammation),
plaster containing Vitamin A acid as the active agent (to counter keratosis),
plaster containing antibiotic as the active agent (to counter infectious diseases),
plaster containing an antithrombotic as the active agent (to counter thrombosis).

A further exemplary embodiment is illustrated in the scope of the same figure. In this case the molecular sieve having a uniform degree of dehydration is loaded with a first active agent $Z_1$, and a second active agent $Z_2$, which are present in different degrees of loading, so that molecular sieve/active agent adduct 5 releases active agents $Z_1$, and $Z_2$ sequentially upon skin contact 6 of active membrane 3, as illustrated by the different arrow thicknesses. The two active agents have approximately the same molecular weight. The following numerical example will illustrate this. The molecular sieve has a degree of dehydration of 70%. At a total degree of loading with active agents $Z_1$, and $Z_2$ equal to 60%, $Z_1$, accounts for 40% and $Z_2$ for 20%. By virtue of the greater loading concentration, active agent $Z_1$, is released more rapidly than active agent $Z_2$, and therefore the therapeutic effects are staggered in time.

Figure 2:
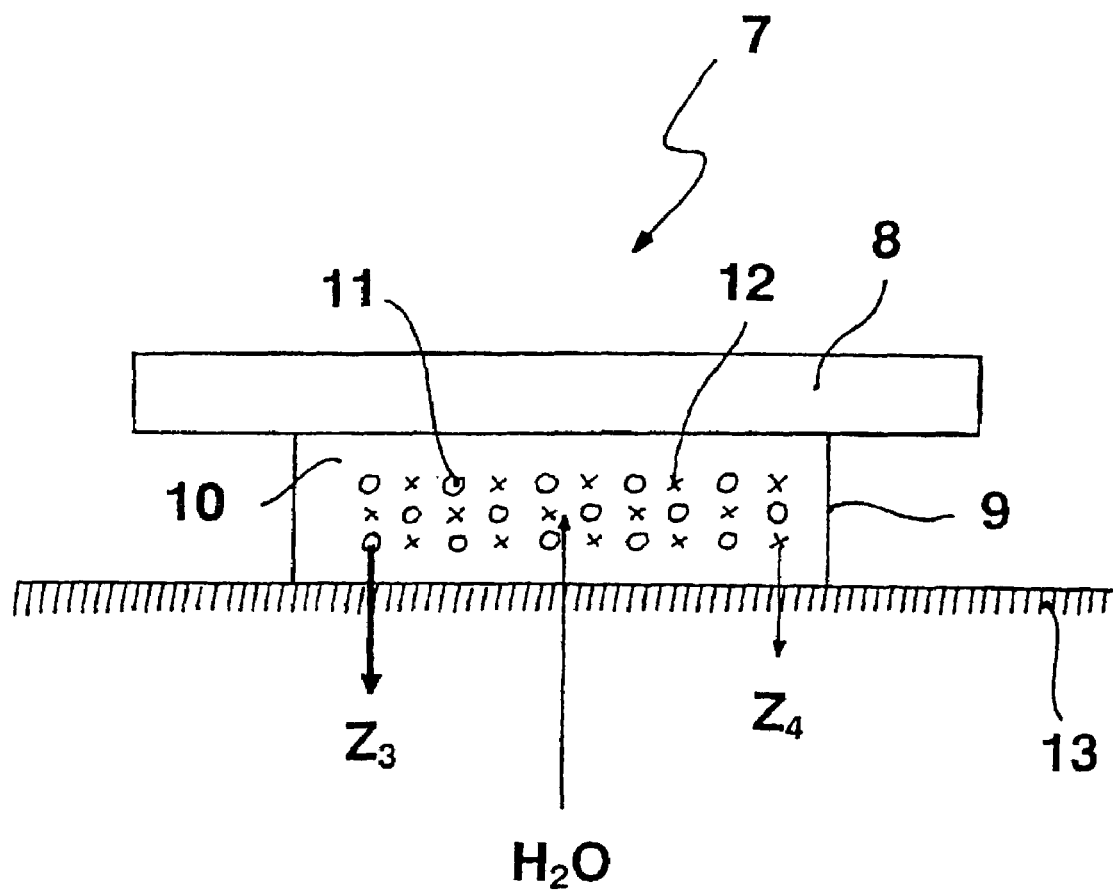
FIG. 2 shows the adsorption/desorption mechanism on the basis of two molecular sieve/active agent adducts which have different degrees of dehydration.

An example of a medical use of this type would be the combination of an antithrombotic ($Z_1$) with an antibiotic ($Z_2$), which can also be cited for the exemplary embodiment according to FIG. 2, which will now be presented in more detail.

A first and second molecular sieve 11 and 12 of the same type but different degrees of dehydration are incorporated in matrix 10, as in the following example:
molecular sieve type: $Na_{86}[(AlO_2)_{86} \cdot (SiO_2)_{106}] \cdot m(m')H_2O$
basic molar quantity (m) before partial dehydration: m=276
reduced molar quantity (m')
    molecular sieve/active agent adduct 11 containing active agent $Z_3$: m'=100
    molecular sieve/active agent adduct 12 containing active agent $Z_4$: m'=200

For approximately equal molecular weights of active agents $Z_3$ and $Z_4$, the degree of loading is about the same for each.

Upon skin contact 13 of active membrane 9, active agents $Z_3$ and $Z_4$ are released sequentially, once again as symbolized by the arrows of different thickness. In other words, adduct 11 with the greater degree of dehydration will take up water more readily than adduct 12. As a result, active agent $Z_3$ will be released more rapidly than active agent $Z_4$, and once again the therapeutic effects will be staggered in time.

Independent of the exemplary embodiments, it is practical if the following parameters apply for plasters 1 and 7 containing an active agent:

Adducts 5, 11 and 12 are distributed substantially uniformly in the matrix 4 and 10.
    Adducts 5, 11 and 12 comprise a proportion of 2 to 20 wt %, preferably 5 to 10 wt %, specifically relative to the total mass of active membrane 3 and 9.
Matrix 4 and 10 is a polymer material, especially, once again, an elastomer, a thermoplastic elastomer or a thermoplastic synthetic material. What is important in this connection is that these materials form a skin-compatible matrix.
Active membrane 3 and 9 has a layer thickness of 0.5 mm to 2 mm, preferably 1 mm. The layer thickness of the active membrane is greater than that of the cover membrane.

The plaster containing an active agent is usually enclosed in a sterile package. Alternatively, active membrane 3 and 9 can be covered with a removable protective film.

The values of degree of dehydration and degree of loading cited in the specification and in the claims are relative to the condition after completion of partial dehydration or loading, i.e. before metabolic exchange of water and active agent.

LIST OF REFERENCE SYMBOLS

1 Plaster containing an active agent
2 Cover membrane
3 Active membrane
4 Matrix
5 Molecular sieve/active agent adduct containing active agents Z, $Z_1$, $Z_2$
6 Skin contact
7 Plaster containing an active agent
8 Cover membrane
9 Active membrane
10 Matrix
11 Molecular sieve/active agent adduct containing active agent $Z_3$
12 Molecular sieve/active agent adduct containing active agent $Z_4$
13 Skin contact

The invention claimed is:
1. Plaster containing an active agent (1, 7) comprising at least
    one cover membrane (2, 8) and
    an active membrane (3, 9) based on a skin-compatible matrix (4, 10), containing a molecular sieve which is loaded with at least one active agent (Z, $Z_1$, $Z_2$, $Z_3$, $Z_4$), wherein the molecular sieve/active agent adduct (5, 11, 12), releases the active agent upon skin contact (6, 13) of the active membrane, in conjunction with the transpired water of the skin, characterized in that
  the molecular sieve/active agent adduct (5, 11, 12) also contains water of crystallization, to the extent that the molecular sieve is partially dehydrated at a degree of dehydration of at least 20%, compared to a sufficient basic molar quantity (m) of water of crystallization of at least 100, said molecular sieve with the reduced molar quantity (m') of water of crystallization being loaded with the active agent (Z, $Z_1$, $Z_2$, $Z_3$, $Z_4$), so that water is adsorbed upon skin contact (6, 13) of the active membrane (3, 9) and the active agent is desorbed, whereupon the water of crystallization content of the molecular sieve increases, and
  the molecular sieve is a sodium aluminosilicate of the following formula:

$$Na_{86}[(AlO_2)_{86} \times (SiO_2)_{106}] \times m(m')H_2O.$$

2. Plaster containing an active agent according to claim 1, characterized in that the molecular sieve contains a basic molar quantity (m) of water of crytallization equal to at least 200.

3. Plaster containing an active agent according to claim 1, characterized in that the molecular sieve is a sodium aluminosilicate of the following formula:

$$Na_{86}[(AlO_2)_{86} \times (SiO_2)_{106}] \times 276\, H_2O.$$

4. Plaster containing an active agent according to claim 1, characterized in that the partially dehydrated molecular sieve has a degree of dehydration of 40 to 70%.

5. Plaster containing an active agent according to claim 1, characterized in that the degree of loading of the active agent (Z, $Z_1$, $Z_2$, $Z_3$, $Z_4$) in the molecular sieve/active agent adduct (5, 11, 12) is smaller than the degree of dehydration of the partially dehydrated molecular sieve.

6. Plaster containing an active agent according to claim 5, characterized in that the degree of loading is equal to at least 50% of the degree of dehydration.

7. Plaster containing an active agent according to claim 1, characterized in that the molecular sieve/active agent adduct (5, 11, 12) is distributed substantially homogeneously within the matrix (4, 10) of the active membrane (3, 9).

8. Plaster containing an active agent according to claim 1, characterized in that the molecular sieve/active agent adduct (5, 11, 12) is present in a proportion of 2 to 20 w t%, specifically relative to the total mass of the active membrane (3, 9).

9. Plaster containing an active agent according to claim 1, characterized in that the matrix (4, 10) of the active membrane (3, 9) is a polymer material, such as an elastomer, a thermoplastic elastomer or a thermoplastic synthetic material.

10. Plaster containing an active agent according to claim 1, characterized in that the active membrane (3, 9) has a layer thickness of 0.5 mm to 2 mm.

11. Plaster containing an active agent according to claim 1, characterized in that the active membrane (3, 9) has a greater layer thickness than the cover membrane (2, 8).

12. Plaster containing an active agent according to claim 1, characterized in that the molecular sieve having a uniform degree of dehydration is loaded with at least a first active agent ($Z_1$) and a second active agent ($Z_2$), which are present in different degrees of loading, so that the molecular sieve/active agent adduct (5) releases the active agents ($Z_1$, $Z_2$) sequentially upon skin contact (6) of the active membrane (3).

13. Plaster containing an active agent according to claim 1, characterized in that at least a first and second molecular sieve of the same type but different degress of dehydration are incorporated in the matrix (10), the first molecular sieve being loaded with a first active agent ($Z_3$) and the second molecular sieve being loaded with a second active agent ($Z_4$), specifically having the same degree of loading, so that the first molecular sieve/active agent adduct (11) and the second molecular sieve/active agent adduct (12) release the active agents ($Z_3$, $Z_4$) sequentially upon skin contact (13) of the active membrane (9).

14. Plaster containing an active agent according to claim 1, characterized in that the active membrane (3, 9) is self-adhesive.

15. Plaster containing an active agent according to claim 14, characterized in that the self-adhesive capability of the active membrane (3, 9) is based on a self-adhesive matrix (4, 10).

16. Plaster containing an active agent according to claim 14, characterized in that the molecular sieve/active agent adduct (5, 11, 12) is prepared in such a way that it triggers the self-adhesive capability of the active membrane (3, 9) in combination with a non-adhesive matrix (4, 10).

17. A method for the production of a plaster containing an active agent (1, 7) according to claim 1, characterized by the following steps:
  the molecular sieve with a sufficient basic molar quantity (m) of water of crystallization is partially dehydrated at 300 to 500° C., for 2 to 6 hours;
  the partially dehydrated molecular sieve with the reduced molar quantity (m') of water of crystallization is then loaded with at least one active agent (Z, $Z_1$, $Z_2$, $Z_3$, $Z_4$), thereby forming the molecular sieve/active agent adduct (5, 11, 12);
  the molecular sieve/active agent adduct (5, 11, 12) is now incorporated into the matrix (4, 10) to form the active membrane (3, 9);
  finally, the active membrane (3, 9) is assembled with the cover membrane (2, 8) to form the plaster containing an active agent (1, 7).

18. Method according to claim 17, characterized in that the dehydration and/or loading step(s) is/are performed in the presence of an inert gas.

19. Method according to claim 17, characterized in that the dehydration and/or loading step(s) is/are performed under normal pressure.

20. Method according to claim 17, characterized in that it is followed by a drying process.

21. Method according to claim 20, characterized in that the drying process is carried out at 30 to 100° C., for 2 to 6 hours.

* * * * *